(12) United States Patent
Moss

(10) Patent No.: US 6,200,556 B1
(45) Date of Patent: Mar. 13, 2001

(54) HIGH FIBRE, LOW CALORIE, DIETARY COMPOSITION

(76) Inventor: Clive B. Moss, c/0 111-1537. Belcher Avenue, Victoria, British Columbia (CA), V8R 4N2

(*) Notice: Subject to any disclaimer, the term of this patent is extended or adjusted under 35 U.S.C. 154(b) by 0 days.

(21) Appl. No.: 09/265,813

(22) Filed: Mar. 10, 1999

Related U.S. Application Data

(63) Continuation-in-part of application No. 09/016,939, filed as application No. PCT/CA96/00564 on Aug. 22, 1996, now abandoned.

(30) Foreign Application Priority Data

Aug. 22, 1996 (WO) .................................. PCT/CA96/00564

(51) Int. Cl.⁷ ............................ A61K 31/74; A23L 1/308
(52) U.S. Cl. ....................... 424/78.01; 424/400; 424/489; 426/804
(58) Field of Search .................................... 424/400, 489, 424/78.01; 426/804; 514/867

(56) References Cited

U.S. PATENT DOCUMENTS 5,213,806 * 5/1993 Ito et al. .

FOREIGN PATENT DOCUMENTS 59 080 608 * 5/1984 (JP) .
01 319 421 * 12/1989 (JP) .

\* cited by examiner

*Primary Examiner*—Thurman K. Page
*Assistant Examiner*—Brian K. Seidleck
(74) *Attorney, Agent, or Firm*—Terry M Gernstein

(57) ABSTRACT

A food formulation comprising an edible alkyl, or substituted alkyl cellulose compound and an edible polyhydric alcohol is provided which in combination and in specified amounts have been found to synergistically attain progressive, controlled hydration thereof during passage through the digestive system. The formulation may be further provided with a time-release coating thereover.

3 Claims, No Drawings

HIGH FIBRE, LOW CALORIE, DIETARY COMPOSITION

CROSS REFERENCE TO RELATED APPLICATION

This application is a continuation-in-part of application Ser. No. 09/016,939 filed as PCT/CA96/00564 on Aug. 22, 1996 now abandoned.

FIELD OF THE INVENTION

The present invention relates to a high fibre, low fat, low calorie natural food formulation usable on its own, in admixture with raw foodstuffs or as an ingredient in cooked or frozen food. The formulation is effective as a weight loss promoting dietary product having the long-recognized high vegetable food regimen anti-constipation effects during normal physiological passage through the gastrointestinal canal with ultimate voiding.

BACKGROUND OF THE INVENTION

In the more civilized and affluent countries of the world, the problem of obesity, both numerically and in degree, is a continually rising and unabated trend. Generally, this is a result of increased mechanization concomitant with decreased human physical activity combined with an increasing ready availability of inexpensive, appetizing, high calorific, inexpensive foods.

Since the time of Hippocrates, in Ancient Greece some 2,300 years ago, medicinal beliefs have held that mild and definitely more accentuated obesity is deleterious, if not fatal, to an individual's quality of health and length of life. Not only, therefore, does obesity give rise to serious individual health concerns but it also has major effects on national and international health and so world wide socio-economic issues.

The causes of obesity are twofold:

1) regulatory obesity:

This is by far the more prevalent (approximately 95%) and has no disease metabolic abnormality origins, the cause being the intake of a greater calorie content food than that which is required by the body. Consequently, the management of the appetite and so food and calorie intake is the personal responsibility of the individual.

2) metabolic obesity:
   a comparatively uncommon cause which is a true disease process resulting from endocrine disorders that disrupt the body's normal inherent metabolic processes. Metabolic obesity requires medical management.

Restriction of calorie intake to below that of energy expenditure is the only way to reduce regulatory obesity and so body weight. This weight loss may be attained, without using surgical techniques, by following a predetermined diet or using a dietary aid either alone or in conjunction with a selected diet. However, the successful utilization of a diet alone is difficult and requires much discipline. The slowness in obtaining results is often so discouraging that diet plans are frequently abandoned.

Dietary aids which are readily available commercially may be broadly classified as either reduced calorie foods or as drug appetite suppressants.

It is essential when dieting, or indeed at any time, to prevent deviation from normal bodily functions which, if altered significantly, may lead to illness or death. An example would be the use of a liquid or low fibre diet, which would deprive the intestine of the solid content necessary for effective physiological and mechanical function, thus potentially causing damage thereto and, ultimately, to various benign and/or malignant disease processes of the small bowel and colon downstream.

In designing a weight reducing diet one must introduce reduced calorie content natural foodstuff(s) having a physiological and so natural, healthy passage through the length of the gastrointestinal canal. Most preferably, such a nutrition scheme would have a low calorie, high fibre and low fat content. Clearly the dietary aid must satisfy hunger and appetite senses, whilst providing complete emotional and physical appetite satisfactions of sight, smell, hearing, taste and palatability senses.

A common gastrointestinal tract problem is constipation, which occurs in all age groups but is both more common and more serious among the senior citizen age group. Often the causes of constipation are difficult to diagnose and frequently involve expensive and time consuming physician consultations, investigations, hospitalizations, treatments and/or medications.

SUMMARY OF THE INVENTION

It is a primary objective of the present invention to provide a low calorie, high fibre, low fat food formulation which primarily and functionally is a dietary food promoting obesity reduction and so, prospectively, a healthier, happier, longer and more productive life. The high fibre content maintains normal intestinal functions with prophylaxis against constipation and with medically recognised reduced incidences of both benign and malignant disease processes in all systems of the body.

It is a further objective of the invention to provide a product which contains physiological quantities of edible yet virtually indigestible artificial cellulose compounds which are ingested by mouth and made available to the digestive system at predetermined locations therein. For example, in a product being used as a dietary aid, the cellulose compound is designed to be partially hydrated in the stomach to satisfy the mechanical hunger sensations. The cellulose compound, because of its specific formulation, reaches full hydration equilibrium in the colon and so precludes constipation development and/or relieves established dietary constipation. The anti-constipation effects are obviously also an intrinsic benefit of the anti-obesity usages.

By providing a essentially indigestible compound there is virtually no calorie intake therefrom yet at the same time the product provides all the emotional and physical well-being generated by the ingestion of food and by the prevention and/or the relief of constipation. The product is such that the cellulose derivative(s) ingested has very limited initial hydration when wetted in the mouth, oesophagus and stomach. The nature of the product controls this hydration in such a manner as to allow free passage of the cellulose ingested through the mouth, oesophagus, stomach, and so through the small intestine to the colon for retention prior to voiding from the colon.

This objective is realized by the discovery and application, that there is a synergistic effect between the combination, in specified amounts, of the provision of an edible, cellulose derivative and an edible polyhydric alcohol whereby progressive, controlled hydration of said cellulose derivative through the entire gastrointestinal canal from eating to colon voiding.

In accordance with the present invention there is provided a dietary composition comprising a mixture of an edible alkyl or substituted alkyl cellulose compound selected from methyl cellulose, ethyl cellulose, methyl-ethyl cellulose, sodium carboxy methyl cellulose, other derivatives of cellulose or mixtures thereof; and an edible polyhydric alcohol. Preferably, the cellulose compound is present in an amount of about 100 parts by weight and the polyhydric alcohol is present in an amount of from about 100 to 175 parts by weight or stated otherwise, the cellulose compound is provided in an amount of about 30 to 50 weight percent cellulose compound and about 50 to 75 weight percent polyhydric alcohol.

Any suitable edible polyhydric alcohol may be utilized; however, sorbitol or glycerol are preferred.

The invention extends to a second embodiment wherein there is provided a food formulation having a time-release coating component which functionally controls the rate of hydration of the active cellulose ingredient of the formulation comprising a mixture of an alkyl or substituted alkyl edible cellulose compound selected from methyl cellulose, ethyl cellulose, methyl-ethyl cellulose, sodium carboxy methyl cellulose, derivatives of cellulose or mixtures thereof and an edible polyhydric alcohol and having an edible time-release coating applied thereto.

Preferably, the time-release coating comprises lecithin but any of several physiologically acceptable slowly dissolving, edible coatings having the desired properties may be utilized. The food/laxative formulation may be prepared by spray coating the time-release compound onto the edible alkyl or substituted alkyl/polyhydric alcohol compound in a conventional manner. As a result, the rate and degree of hydration of the alkyl or substituted alkyl/polyhydric alcohol compound may be controlled as well as the intended timed release thereof.

It is to be noted that, in these compositions, methyl cellulose hydrates more slowly than other cellulose derivatives under the conditions existing within the gastrointestinal canal. Methyl cellulose thus becomes the preferred cellulose compound in the practice of both embodiments of the instant invention.

Thus, the product of the invention may be made available as either the separate ingredients for the user to prepare foods as directed or as the prepared food formulations described supra which are functional both as dietary aids or as a high vegetable content, anti-constipation formulations. Additionally, the formulation may comprise a recipe ingredient in prepared, baked or frozen foods. Typically, the formulation is used as a substitute for between 40to 60% of the flour content of conventional food preparations or recipe ingredients.

Thus a preferred food and/or laxative formulation comprises, but is not limited to, methyl cellulose, and sorbitol and/or glycerol in admixture, and/or with lecithin or other suitable time release coatings.

Beneficially, the compositions of the instant invention are useful in the prophylaxis of constipation and/or faecal compactions resulting from dietary preconditions having a shortage of fibre/vegetable content in the food intake, such conditions being most common with the senior citizen age group.

Broadly stated the invention is an indigestible dietary composition orally administered to the gastrointestinal canal which is functional to progressively hydrate therethrough comprising a mixture of an edible alkyl or an edible substituted alkyl cellulose compound selected from the group consisting of methyl cellulose, ethyl cellulose, methyl-ethyl cellulose, sodium carboxy methyl cellulose, derivatives of cellulose or mixtures thereof wherein said cellulose compound comprises about 100 parts by weight; and an edible polyhydric alcohol, said polyhydric alcohol comprising from about 100 to 175 parts by weight.

In a second broad aspect the invention extends to a food formulation comprising an edible alkyl or edible substituted alkyl cellulose compound selected from the group consisting of methyl cellulose, ethyl cellulose, methyl-ethyl cellulose, sodium carboxy methyl cellulose, derivatives of cellulose or mixtures thereof; an edible polyhydric alcohol; and having a time-release coating thereover.

Thirdly, the invention broadly encompasses a method for preventing dietary intestinal constipation in a patient which comprises: administering to a patient a composition which comprises a mixture of an edible alkyl or edible substituted alkyl cellulose compound selected from the group consisting of methyl cellulose, ethyl cellulose, methyl-ethyl cellulose, sodium carboxy methyl cellulose, derivatives of cellulose or mixtures thereof wherein said cellulose comprises about 100 parts by weight ; and an edible polyhydric alcohol, said polyhydric alcohol comprising from about 100 to 175 parts by weight.

DESCRIPTION OF THE PREFERRED EMBODIMENT

Cellulose compounds which may be used, if desired, are alkyl ethers of cellose and substitution products thereof. Physiological considerations and possible toxicity of certain cellulose derivatives limit the number and type of such cellulose compounds which are suitable for use in this invention. Taking into consideration these factors, it has been found that, generally, any cellulose derivative which is edible and non-toxic may be used for the purposes of the present invention provided that the hydration rate of the cellulose derivative in the mouth, oesophagus, stomach and small and large intestine can be controlled by simultaneously administered natural foods with osmotic properties appropriately controlling the cellulose derivatives hydration rates.

Generally, the cellulose derivatives which have been found to have preferred properties for the compositions of this invention are those in which methyl and/or ethyl radicals are substituted at given intervals along the cellulose chains. It has been found that there is a correlative relationship between the type of alkyl substitution in a cellulose molecule and the hydration rate of the cellulose derivative within the human gastrointestinal canal; the simpler the substitution, the slower the hydration rate and, conversely, the more complex the substitution the faster the hydration rate.

For the purposes of the present invention it is most desirable that the cellulose derivative having a relatively slow rate of hydration be employed. Accordingly, as methyl cellulose derivatives hydrate more slowly than other cellulose derivatives under the conditions within the human mouth, oesophagus and stomach for this basic reason, methyl cellulose is the preferred edible cellulose derivative for use in the dietary/laxative compositions of the invention.

The polyhydric alcohol to be used is selected on the basis of its hydrophillic and other physical and chemical properties and also on the basis of physiological considerations, (such as, e.g. osmotic capability or toxicity). The physical and chemical properties of all polyhydric alcohols (which are compounds containing from two to six hydroxyl groups substituted in a paraffin, hydrocarbon residue) are basically similar. However, because of their specific physical and chemical properties, as well as proven safety by long usage in medicine and culinary fields, sorbitol and glycerol or a mixture of these are preferred polyhydric alcohols for use in compositions of the present invention. The most preferred polyhydric alcohol is sorbitol, which has long been accepted and used as a safe food and pharmacological substance. One great advantage in the use of sorbitol is reputedly that it has been reported that in excess of 90% of sorbitol ingested by mouth is not converted into glucose in the body, consequently no clinically significant disturbance of the blood sugar levels occurs. Moreover, sorbitol is not significantly attacked by weak acids or alkalis and so, for practical purposes, is stable within the gastrointestinal canal.

Glycerol is also an acceptable polyhydric alcohol for use in the composition of this invention. This substance is a long established food and/or pharmacological agent and is known to be safe. However, it does not have the desired physical and chemical properties to the same degree as sorbitol and so is less favourable for the purposes of the invention.

Numerous other polyhydric alcohols, some of which are artificially produced and others of which are produced by extraction from various natural sources, may be used in the compositions of the invention. Among these there may be listed the following: arabitol, orthritol, mannitol, and the alcohols of such sugars as alose, altrose, talose, galactose, sorbose, xylose, ribose, rhamnose, fructose or the like.

The mixture for the preparation of the basic dietary composition is obtained by adding 100 parts by weight of cellulose compound to about 125 to 175 parts by weight of polyhydric alcohol.

The polyhydric alcohol(s) coats and saturates the cellulose grains and competes with the cellulose for water and denies cellulose access to available water in the mouth, oesophagus and stomach. Uptake of water by the cellulose does not begin until an approximate concentration of 10% or more alcohol in water is reached. This point at which hydration of the cellulose compound begins can be controlled by varying either the nature and/or amount of the polyhydric alcohol(s) in the composition.

The time-release coating comprises any suitable slowly dissolving edible coating having the desired properties. The preferred coating comprises lecithin. Lecithin has a well known lipotrophic and liposolvent property which medically is recognised as protective and, some say, prophylactic against -the formation of or, even curative of, established cardiovascular obliterative arterial lipid depositions. The food formulation may be prepared by spray coating the time-release compound onto the alkyl or substituted alkyl edible compound in a conventional manner. Alternatively the alkyl or substituted alkyl edible compound may additionally be treated with an edible polyhydric alcohol to thereby impart some partial or total degree of control to the rate of hydration. The thickness of the coating required will be easily determined by one skilled in the art having regard to the target site of physiological action within the gastrointestinal canal.

The following non-limitative examples illustrative of the invention are given herebelow.

EXAMPLE 1

A dietary formulation having the following composition:
60 g methyl cellulose
75–125 g polyhydric alcohol
0.1 g sodium benzoate; and
flavouring and colouring as required.

Examples 2 to 6 are further formulations which may be used in the practice of the present invention.

EXAMPLE 2

60 g methyl cellulose
37.5 g sorbitol
37.5 g glycerol
0.1 g sodium benzoate

EXAMPLE 3

45 g methyl cellulose
10 g ethyl cellulose
50 g sorbitol
25 g glycerol
0.1 g sodium benzoate

EXAMPLE 4

40 g methyl cellulose
10 g hydroxy-methyl cellulose
10 g carboxy-ethyl cellulose
75 g sorbitol
0.1 sodium benzoate

EXAMPLE 5

60 g methyl cellulose
37.5 g sorbitol
37.5 g glycerol
0.1 sodium benzoate

EXAMPLE 6

45 g methyl cellulose
10 g ethyl cellulose
60 g sorbitol
15 g glycerol
0.1 g sodium benzoate

What is claimed is:

1. An indigestible dietary composition orally administered to the gastrointestinal canal which is functional to progressively hydrate therethrough comprising a mixture of an edible alkyl or an edible substituted alkyl cellulose compound selected from the group consisting of methyl cellulose, ethyl cellulose, methyl-ethyl cellulose, sodium carboxy methyl cellulose, or mixtures thereof wherein said cellulose compound comprises about 100 parts by weight; and an edible polyhydric alcohol selected from sorbitol or glycerol or mixtures thereof, said polyhydric alcohol comprising from about 100 to 175 parts by weight.

2. A food formulation comprising an edible alkyl or edible substituted alkyl cellulose compound selected from the group consisting of methyl cellulose, ethyl cellulose, methyl-ethyl cellulose, sodium carboxy methyl cellulose, or mixtures thereof; an edible polyhydric alcohol selected from sorbitol or glycerol or mixtures thereof, said polyhydric alcohol comprising from about 100 to 175 parts by weight; and having a time-release coating thereover.

3. A method of treatig dietary intestinal constipation in a patient which comprises:
   administering to a patient a composition which comprises a mixture of an edible alkyl or edible substituted alkyl cellulose compound selected from the group consisting of methyl cellulose, ethyl cellulose, methyl-ethyl cellulose, sodium carboxy methyl cellulose, or mixtures thereof wherein said cellulose comprises about 100 parts by weight; and an edible polyhydric alcohol selected from sorbitol or glycerol or mixtures thereof, said polyhydric alcohol comprising from about 100 to 175 parts by weight.

* * * * *